(12) United States Patent
Neal et al.

(10) Patent No.: US 11,180,735 B2
(45) Date of Patent: Nov. 23, 2021

(54) METHODS TO PRESERVE TUMOR-STROMAL INTERACTIONS IN CULTURE AND THERAPEUTIC PREDICTIVE APPLICATIONS THEREOF

(71) Applicant: The Board of Trustees of the Leland Stanford Junior University, Stanford, CA (US)

(72) Inventors: James Neal, San Mateo, CA (US); Calvin Jay Kuo, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 56 days.

(21) Appl. No.: 15/793,249

(22) Filed: Oct. 25, 2017

(65) Prior Publication Data

US 2018/0119107 A1 May 3, 2018

Related U.S. Application Data

(60) Provisional application No. 62/414,549, filed on Oct. 28, 2016.

(51) Int. Cl.
| | |
|---|---|
| C12N 5/09 | (2010.01) |
| A61K 39/395 | (2006.01) |
| C12N 5/0783 | (2010.01) |
| G01N 33/574 | (2006.01) |
| C07K 16/28 | (2006.01) |
| G01N 33/50 | (2006.01) |
| A61K 39/00 | (2006.01) |

(52) U.S. Cl.
CPC ...... *C12N 5/0693* (2013.01); *A61K 39/39558* (2013.01); *C07K 16/2818* (2013.01); *C12N 5/0636* (2013.01); *G01N 33/5011* (2013.01); *G01N 33/5047* (2013.01); *G01N 33/57484* (2013.01); *A61K 2039/505* (2013.01); *G01N 2800/50* (2013.01)

(58) Field of Classification Search
CPC .. C12N 5/0634; C12N 5/0636; C12N 5/0639; A61K 39/39558; G01N 33/5047; G01N 33/574; G01N 33/57484
USPC ...................................................... 435/7.23
See application file for complete search history.

(56) References Cited

U.S. PATENT DOCUMENTS

| | | | |
|---|---|---|---|
| 8,642,339 B2 | 2/2014 | Sato et al. | |
| 9,464,275 B2 | 10/2016 | Kuo et al. | |
| 10,704,026 B2 * | 7/2020 | Kuo | G01N 33/5073 |
| 2003/0166274 A1 | 9/2003 | Hewitt et al. | |
| 2004/0023415 A1 | 2/2004 | Sokolov et al. | |
| 2004/0175367 A1 | 9/2004 | Herlyn et al. | |
| 2005/0256036 A1 | 11/2005 | Boyle et al. | |
| 2010/0047853 A1 * | 2/2010 | Kuo | C12N 5/0679 435/34 |
| 2012/0321666 A1 * | 12/2012 | Cooper | A61K 39/0011 424/278.1 |

FOREIGN PATENT DOCUMENTS

| | | |
|---|---|---|
| WO | 2003/023018 A2 | 3/2003 |
| WO | 2006/136953 A2 | 12/2006 |
| WO | 2008/088524 A2 | 7/2008 |
| WO | 2010/090513 A2 | 12/2010 |

OTHER PUBLICATIONS

Wu et al. (Cancer J. 2012, vol. 18(2): 160-175).*
Kim et al., "Mitogenic Influence of Human R-Spondin1 on the Intestinal Epithelium", Science, Aug. 19, 2005, pp. 1256-1259, vol. 309, Issue 5738, American Association for the Advancement of Science, Washington, D.C.
Sambruy et al., "Intestinal Cell Culture Models", Cell Biology and Toxicology, 2001, pp. 301-317, vol. 17, Kluwer Academic Publishers, Dordrecht, Netherlands.
Li et al., "Oncogenic transformation of diverse gastrointestinal tissues in primary organoid culture", Nature Medicine, Jul. 2014, pp. 769-777, 20(7), Macmillan Publishers Limited, Basingstoke, United Kingdom.
Toda et al., "Culture Models for Studying Thyroid Biology and Disorders", ISRN Endocrinology, 2011, vol. 2011, Article ID 275782, pp. 1-9, Hindawi, Cairo, Egypt.
Bartsch et al., "Establishment of a Long-Term Culture System for Rat Colon Epithelial Cells", In Vitro Cell Dev Bioi. Anim., Oct. 2004, pp. 278-284, 40(889), BioOne Complete, Washington, D.C.
Baten et al., "Long-term Culture of Norman Human Clonic Epithelial Cells In Vitro", The FASEB Journal, Jun. 1992, pp. 2726-2734, 6(9), National Center for Biotechnology Information, Bethesda, MD.
Macartney; et al., "Primary Murine Small Intestinal Epithelial Cells, Maintained in Long-Term Culture, Are Susceptible to Rotavirus Infection", Jour. of Virology, Jun. 2000, pp. 5597-5603, 74(12), American Society for Microbiology, Washington, D.C.
Oottani et al., "Sustained In Vitro Intestinal Epithelial Culture Within a Wnt-Dependent Stem Cell Niche." Nat. Med., Jun. 2009, pp. 701-706, 15(6), Macmillan Publishers Limited, Basingstoke, United Kingdom.
Panja, "A Novel Method for the Establishment of a Pure Population of Nontransformed Human Intestinal Primary Epithelial Cell (HIPEC) Lines in Long Term Culture", Lab Invest., Sep. 2000, p. 1473-1475, 80(9), Macmillan Publishers Limited, Basingstoke, United Kingdom.
Rizvi et al., "Epithelial Stem Cells and Their Niche: There's No Place Like Home", Stem Cells, Feb. 1, 2005, pp. 150-165, 23, John Wiley & Sons, Inc., Hoboken, NJ.
Sambuy et al., "Formation of Organoid Structures and Extracellular Matrix Production in an Intestinal Epithelial Cell Line During Long-Term In Vitro Culture", Cell Differ, Sep. 1986, pp. 139-147, vol. 19, Issue 2, Elsevier, Amsterdam, Netherlands.

(Continued)

*Primary Examiner* — Yan Xiao
(74) *Attorney, Agent, or Firm* — Pamela J. Sherwood; Boziecvic, Field & Francis LLP

(57) ABSTRACT

Functional in vitro assays are provided for determining patient specific responsiveness to immunotherapy agents within a clinically actionable time frame.

9 Claims, 13 Drawing Sheets

(13 of 13 Drawing Sheet(s) Filed in Color)

(56) References Cited

OTHER PUBLICATIONS

Toda et al., "Thyroid Tissue-Organotypic Culture Using a New Approach for Overcoming the Disadvantage of Conventional Organ Culture", Cell Biology, 2005, A Laboratory Handbook, vol. 1, Chapter 50, 4 pages, Elsevier, Amsterdam, Netherlands.

Toda et al., "A new Organotypic Culture of Thyroid Tissue Maintains Three-Dimensional Follicles with C Cells for a Long Term", Bio. Biophysical Research Comm., Jul. 2002, pp. 906-911, 294, Elsevier, Amsterdam, Netherlands.

Toda et al., "Air Exposure Promotes Fibroblast Growth with Increased Expression of Mitogen-Activated Protein Kinase Cascade", Bio. Biophysical Research Comm, 2000, pp. 961-966, 270, Academic Press, Cambridge, MA.

Fulcher et al., "Well-differentiated human airway epithelial cell cultures", Methods of Molecular medicine, 2005, pp. 183-206, vol. 107, Humana Press, New York City, NY.

Tou et al., "Regulation of Mammalian Epithelial Differentiation and Intestinal Development by Class I Histone Deacetylases", Molceular and Cellular Biology, Apr. 2004, pp. 3132-3139, vol. 24, No. 8, American Society for Microbiology, Washington, D.C.

Ootaini et al., "An Air-Liquid Interface Promotes the Differentiation of Gastric Surface Mucous Cells (GSM06) in Culture", Biochemical and Biophysical Research Communications, May 19, 2000, pp. 741-746, vol. 271, Issue 3, Elsevier, Amsterdam, Netherlands.

Fletcher et al., "Ex vivo culture of human colorectal tissue for the evaluation of candidate microbicides", AIDS, Jun. 12, 2006, pp. 1237-1245, vol. 20—Issue 9, Wolters Kluwer Health, Inc., Philadelphia, PA.

Quinlan et al., "In vitro culture of embryonic mouse intestinal epithelium: cell differentiation and introduction of reporter genes", BMC Developmental Biology, May 2006, pp. 1-11, 6(24), BioMed Central, London, United Kingdom.

Benbrook, "Organotypic cultures represent tumor microenvironment for drug testing", Drug Discovery Today Disease Model, Summer 2006, pp. 143-148, vol. 3, Issue 2, Elsevier, Amsterdam, Netherlands.

Froeling et al., "Pancreatic cancer organotypic cultures", Journal of Biotechnology, Jul. 1, 2010, pp. 16-23, vol. 148, Issue 1, Elsevier, Amsterdam, Netherlands.

Dobbs et al., "Maintenance of the differentiated type II cell phenotype by culture with an apical air surface", Am J Physiol., Aug. 1997, Pages L347-L354, 273(2 Pt 1), American Physiological Society, Bethesda, MD.

Driscoll et al. "Characterizing Mutagenesis in the HPRT Gene of Rat Alveolar Epithelial Cells", Exp Lung Res Nov.-Dec. 1995, pp. 941-956, 21(6), Abstract only attached, Informa UK Limited, London, United Kingdom.

Knowles et al. "Long-term organ culture of normal human bladder", Cancer Res., Jan. 1983, pp. 374-385, 43(1); American Association for Cancer Research, Philadelphia, PA.

Yamaya et al., "Differentiated structure and function of cultures from human tracheal epithelium", Am J Physiol., Jun. 1, 1992, pp. L713-L724, vol. 262 No. 6, American Journal of Physiology, Bethesda, MD.

Hogenesch et al., "Challenges in pre-clinical testing of anti-cancer drugs in cell culture and in animal models", J. Control Release, Dec. 10, 2012, pp. 183-186, 164(2), Elsevier, Amsterdam, Netherlands.

\* cited by examiner

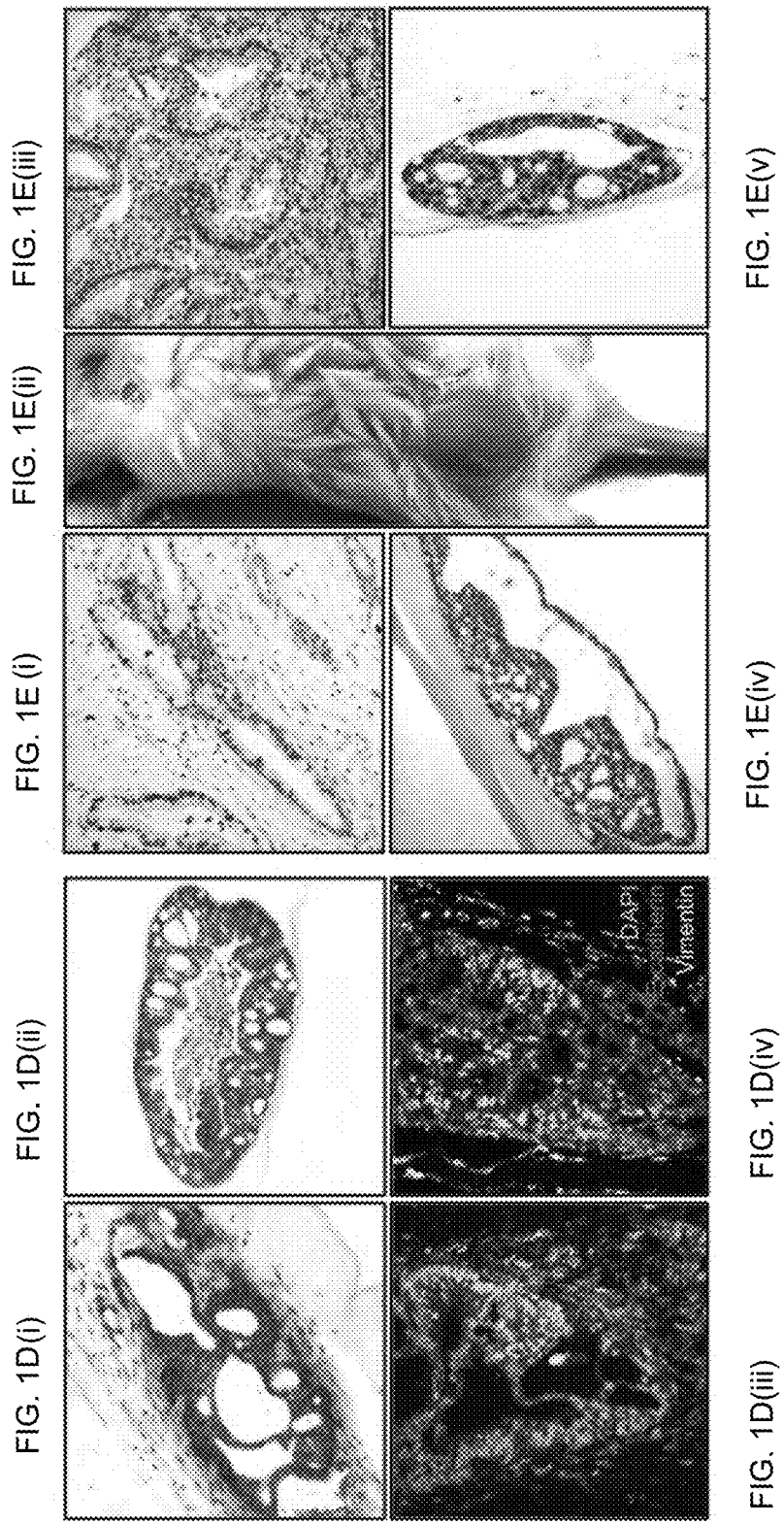

METHODS TO PRESERVE TUMOR-STROMAL INTERACTIONS IN CULTURE AND THERAPEUTIC PREDICTIVE APPLICATIONS THEREOF

CROSS REFERENCE

This application claims benefit of U.S. Provisional Patent Application No. 62/414,549, filed Oct. 28, 2016, which application is incorporated herein by reference in its entirety.

FEDERALLY SPONSORED RESEARCH AND DEVELOPMENT

This invention was made with Government support under contract CA176299 awarded by the National Institutes of Health. The Government has certain rights in the invention.

BACKGROUND

Numerous studies have documented the vast heterogeneity present in the tumor microenvironment (TME) and the effects of stromal and immune cell types on tumor treatment responses (see Sauvage et al. (2013) Nature 501:346-354). These studies, combined with the recent promise of cancer therapies that exploit this heterogeneity through immune cell activation or other means, have created a particular exigency for human cancer models that recapitulate this diversity. There is, however, a dearth of models, 2-D or 3-D, capable of mimicking the in vivo interaction of tumor and immune cells in the TME.

Current models for tumor/immune co-culture utilize immune cells isolated from blood or patient tumors in combination with established cancer cell line models in a traditional 2-D culture system. Such approaches have yielded data with regard to dendritic cell antigen presentation and the discovery of novel tumor-associated antigens (Feder-Mengus et al. (2008) Trends Mol Med 14:333-340), but fail to recapitulate the full diversity of the tumor microenvironment.

Initial studies in 3-dimensional cell culture utilizing mouse cancer cell spheroids co-cultured with splenocytes showed that immune cells could migrate to and infiltrate these spheroids (Sutherland et al. (1977) J Natl Cancer Inst 58:1849-53). Later studies in which human cancer cell line spheroids were co-cultured with cytotoxic T lymphocytes showed that these lymphocytes could kill tumor cells in vitro, but that cancer cell spheroids exhibited reduced immunogenicity when compared to the same cells grown in 2D (Dangles-Marie et al. (2003) Cancer Res 63: 3682-7).

Additionally, 2-component spheroid studies have also been carried out with tumor cell line spheroids co-cultured with NK cells, monocytes, macrophages and dendritic cells. These studies have convincingly established the existence of altered immune cell responses in 2D vs. 3D culture of the same cell types (Hirt et al. (2014) Adv Drug Deliv Rev 79-80: 145-54) evidencing the need for models of increased spatial and cellular complexity.

Unfortunately, at the present there is no robust in vitro model for the study of tumor immunity that (A) recapitulates the complex physical architecture of a tumor, (B) contains the multiple parenchymal and stromal compartments found in solid tumors, or (C) recapitulates the full complement of tumor-infiltrating lymphocytes (TILs) in these neoplasms. Overall, (D) prior attempts in this area have typically reconstituted tumor cells and immune cells derived separately, rather than co-culturing a primary tumor biopsy from a patient "en bloc" as a cohesive unit containing both tumor cells and matched endogenous tumor-infiltrating lymphocytes that are natively present in a given tumor.

The development of biologically relevant systems for analysis of tumor immunity is of great interest. Such systems are provided herein.

Relevant Literature

A number of publications discuss various methods for culturing different cell types including intestinal epithelial cells. Toda et al in Cell Biology: A Laboratory Handbook, Vol. 1, Chapter 50, describe thyroid tissue-organotypic culture using an approach for overcoming the disadvantages of conventional organ culture. The teachings of the culture methods of Toda et al. are hereby incorporated by reference. Establishment of a long-term culture system for rat colon epithelial cells is described by Bartsch et al. in In Vitro Cell Dev Biol Anim. 2004 September-October; 40(8-9):278-84. Panja et al in Lab Invest. 2000 September; 80(9):1473-5 describe a method for the establishment of a pure population of nontransformed human intestinal primary epithelial cell (HIPEC) lines in long term culture. A method for long-term culture of primary small intestinal epithelial cells (IEC) from suckling mice is described by Macartney et al in J Virol. 2000 June; 74(12):5597-603. Baten et al discuss methods for long-term culture of normal human colonic epithelial cells in vitro. Sambuy; De Angelis I in Cell Differ. 1986 September; 19(2):139-47 describe formation of organoid structures and extracellular matrix production in an intestinal epithelial cell line during long-term in vitro culture. U.S. application Ser. No. 12/545,755 and Ootani et al. in Nat Med. 2009 June; 15(6):701-6 describe a method for long term culture of mammalian intestinal cells and the production of intestinal organoids by this culture method. Yamaya et al. in Am J Physiol. 1992 June; 262(6 Pt 1):L713-24, Dobbs et al. Am J Physiol. 1997 August; 273(2 Pt 1):L347-54, and Fulcher et al. in Methods Mol Med. 2005; 107:183-206 describe the differentiation of tracheal cells, alveolar type II cells, and airway epithelial cells, respectively, in culture.

SUMMARY OF THE INVENTION

Compositions and methods are provided for in vitro culture systems of human solid tumors as 3-dimensional patient derived organoids (PDO) that recapitulate the cellular architecture and ultrastructure of the tumor sample from which they were derived, and include immune cells such as tumor infiltrating lymphocytes, parenchymal and stromal elements. The cultures provide screening assays useful as a functional prognostic to predict a patient's response to cancer therapies, including but not limited to immunotherapies. In some embodiments, an individual determined to be responsive to a cancer therapy is treated accordingly, e.g. by administering an effective dose of an immunotherapy agent. The preclinical efficacy of the immunotherapy agent can also be determined.

In some embodiments, screening assays are provided. In such assays, a PDO culture is initiated with a solid tumor sample. It is shown herein the patient samples, including needle biopsy samples, comprise sufficient stromal and immune cell components to initiate a complex culture comprising these elements. The PDO culture is contacted with a candidate agent of interest for a period of time sufficient to allow an effect on the immune cells, and the effect on the tumor and/or immune cells associated with the tumor are assessed. In some embodiments the candidate agent is an immunotherapeutic agent, including without limitation checkpoint inhibitors; agonists of immune costimulatory molecules; antibodies specific for tumor antigens, which antibodies may activate effector functions on immune cells; activators of innate immune responses; CAR-T cells; etc. The effectiveness of the agent may be monitored by analysis of the immune cells present in the PDO, e.g. by detecting changes in expression of markers associated with immune activation, including but not limited to IFNG, GZMB, PRF1, etc. Effectiveness of the agent may also be functionally measured by the response of immune cells against the PDO tumor cells. The assay can be completed in a clinically actionable time frame, e.g. within about 3 days, within about 5 days, within about 7 days, within about 10 days, e.g. from the time that the agent is brought into contact with the PDO.

Cultures are initiated with fragments of solid tumor tissue ("explants"), which are then cultured embedded in a gel substrate that provides an air-liquid interface. Fragments include biopsy samples, and may be needle biopsy samples. Cultured explants of the invention can be continuously grown in culture for extended periods of time, for example for 1 month or more, e.g. for one year or more. In some embodiments the medium is supplemented with an effective dose of one or more cytokines to enhance the viability of immune cells in the PDO, including without limitation supplementing with an effective dose of IL-2.

On some analyses, the cultures are dissociated after contacting with a candidate agent to measure cell-specific changes. In some embodiments, the cells are analyzed or sorted by flow cytometry, e.g. to separate immune cells from tumor and stromal elements. The immune cells are optionally further sorted or analyzed by specific markers, e.g. CD19, CD3, CD4, CD8, CD119, etc., as appropriate to define an immune cell class, such as T cells, B cells, dendritic cells, macrophages, etc. In some embodiments one or more directly or indirectly labeled antibodies specific for an immune cell marker of interest are bound to the population of dissociated cells for sorting or identification by flow cytometry. In some embodiments the dissociation is enzymatic. In some embodiments the enzyme for dissociation is other than trypsin, including dispase collagenase, liberase, etc. In some embodiments the cells are sorted and the population of interest is analyzed for gene expression, as known in the art and including without limitation qRT-PCR. A preamplification step may be performed for about 5 to about 15 cycles, e.g. greater than about 8, about 10, less than about 15, less than about 12 cycles.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1A-1E(v). Air-liquid interface culture of patient-derived tumor organoids. (FIG. 1A), Air-liquid interface culture schematic. (FIG. 1B), PDO primary culture and re-establishment upon secondary passage. (FIG. 1C), PDOs accurately recapitulate original tumor histology. (FIG. 1D(i)-1D(iv)), Cryopreservation of PDO cultures preserves architecture and epithelial/stromal compartments. Lung PDO culture in primary (FIG. 1D(i), d30) and secondary (FIG. 1D(ii), d21 post-thaw) plating after 3 months in cryostorage. H&E staining (FIG. 1D(i)-1D(ii)) and staining for epithelial (E-cadherin) and stromal (vimentin) cells (FIG. 1D(iii)-1D(iv)) illustrates preservation of fibroblast stroma and architecture before (FIG. 1D(iii)) and after (FIG. 1D(iv)) cryorecovery. (FIG. 1E(i)-1E(v)), PDOs can be xenografted, grown in vivo, and re-derived as ALI organoids. Pancreatic adenocarcinoma original histology (FIG. 1E(i)) is recapitulated in the PDO culture (FIG. 1E(iv)). PDOs grafted in NOG mice (FIG. 1E(ii)) gave rise to adenocarcinoma histology (FIG. 1E(iii)) that was recapitulated in organoids derived from the xenograft (FIG. 1E(v)).

(FIG. 2A), PDO cultures were derived from numerous tumor types and recapitulated a wide range of histological and molecular subtypes (see also Extended Data FIGS. 1-5). (FIG. 2B), Paired live and fixed (hematoxylin and eosin) stained organoids from PDO cultures. Clockwise pairs from top left: colon adenocarcinoma, ampullary adenocarcinoma, salivary gland carcinoma, endometrial adenocarcinoma, lung adenocarcinoma, gastric adenocarcinoma. (FIG. 2C), Successful PDO culture establishment is irrespective of disease stage. Bars represent TNM staging for tumors use to generate PDO cultures. Crosshatched bars indicate unavailable staging information. Each column represents one tumor (tumors without staging information are not displayed). (FIG. 2D), Common genetic alterations sequenced from PDO cultures.

(FIG. 3A), PDOs derived from NSCLC and RCC tumors contain TILs including B-cells, T-cells, NK- and NKT cells. (FIG. 3B), IL-2 supplementation increases organoid T-cell populations. PDOs grown for 7 days in organoid medium or organoid medium supplemented with IL-2. −, no IL-2; +, 600 IU/mL IL-2; ++, 6000 IU/mL IL-2. (FIG. 3C), PDO-infiltrating T-cells can survive for 28 days (longest period examined) or significantly expanded over the same period with IL-2 supplementation (6000 IU/mL). (FIG. 3D-3F), Immunofluorescence staining of human lung adenocarcinoma, renal cell carcinoma and melanoma PDOs showing CD3+ T-cells (gold) closely associated with epithelial cells (purple) in the PDO cultures. (FIG. 3G), Single cell RNA-seq of the FAC-purified CD45+ fraction from a lung adenocarcinoma PDO reveals distinct immune populations including $T_{helper}$, $T_{cytotoxic}$, and $T_{reg}$.

(FIG. 4A), Nivolumab treatment reduces PD-1 FACS signal on PDO TILs due to epitope saturation by nivolumab. (FIG. 4B), quantitative RT-PCR for interferon-gamma (IFNG), granzyme b (GZMB), and perforin 1 (PRF1) in CD3+ TILs from treated and control PDO cultures. (FIG. 4C), T-cell profiling of treated and control PDO cultures matched to ORCHID qRT-PCR results.

DETAILED DESCRIPTION

Figure 1A:
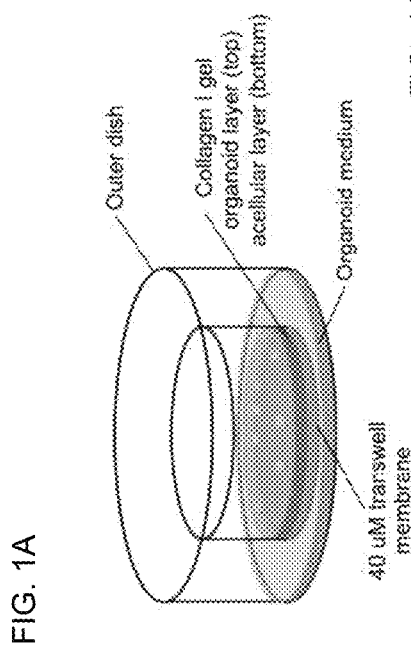

In vitro cancer modeling presents a formidable challenge, as tumor development and progression rely on not only a multiplicity of genetic and molecular alterations, but also physical and spatial factors within a 3-dimensional microenvironment composed of numerous cell types. While recent in vitro models have attempted to integrate tumor architecture by culturing primary human tumors as 3-dimensional spheroids, these models have been composed exclusively of epithelial cells, a reductionist approach that does not recapitulate higher-order phenomena in tumor progression involving stromal and/or immune interactions. Here we present a patient derived organoid (PDO) culture system that accurately recapitulates complex tumor architecture and histology including tumor parenchymal, stromal, and immune compartments without the need for grafting in a non-human host. Using a single 3-dimensional air-liquid interface methodology, a large number of unique PDO cultures from wide variety of human neoplasms.

Histological and genetic characterizations of these PDOs exhibited good concordance with documented clinical pathology and large scale mutational analyses of the tumor types cultured in this study. Further, immunophenotyping analyses of additional lung, melanoma, and kidney PDO cultures revealed the presence of tumor infiltrating lymphocytes including B- and NK-cells in addition to CD4+ and CD8+ T-cells. PDO T-cell populations can be increased in situ by supplementation with IL-2, and T-cell activation and cytolytic activity can be induced in a subset of these PDO cultures by in vitro treatment with an immunotherapeutic agent, for example the anti-PD-1 antibody nivolumab. A useful tool is provided for in vitro investigation into the mechanisms governing human tumor immunity and show that tumor PDO models can be used to predict patient responses to immunotherapy in a clinical setting.

In the description that follows, a number of terms conventionally used in the field of cell culture are utilized extensively. In order to provide a clear and consistent understanding of the specification and claims, and the scope to be given to such terms, the following definitions are provided.

The term "cell culture" or "culture" means the maintenance of cells in an artificial, in vitro environment. It is to be understood, however, that the term "cell culture" is a generic term and may be used to encompass the cultivation not only of individual cells, but also of tissues or organs.

The term "culture system" is used herein to refer to the culture conditions in which the subject explants are grown that promote prolonged tissue expansion with proliferation, multilineage differentiation and recapitulation of cellular and tissue ultrastructure.

"Gel substrate", as used herein has the conventional meaning of a semi-solid extracellular matrix. Gel described here in includes without limitations, collagen gel, matrigel, extracellular matrix proteins, fibronectin, collagen in various combinations with one or more of laminin, entactin (nidogen), fibronectin, and heparin sulfate; human placental extracellular matrix.

An "air-liquid interface" is the interface to which the intestinal cells are exposed to in the cultures described herein. The primary tissue may be mixed with a gel solution which is then poured over a layer of gel formed in a container with a lower semi-permeable support, e.g. a membrane. This container is placed in an outer container that contains the medium such that the gel containing the tissue in not submerged in the medium. The primary tissue is exposed to air from the top and to liquid medium from the bottom, see for example U.S. Pat. No. 9,464,275 herein specifically incorporated by reference.

By "container" is meant a glass, plastic, or metal vessel that can provide an aseptic environment for culturing cells.

The term "explant" is used herein to mean a piece of tumor tissue and the cells thereof originating from the tumor tissue that is cultured in vitro, for example according to the methods of the invention. The tissue from which the explant is derived is obtained from an individual, i.e. a cancer patient. Methods of interest include patient-specific analysis of anti-tumor immune responses.

The term "organoid" is used herein to mean a 3-dimensional growth of tumor tissue in culture that retains characteristics of the tumor in vivo, e.g. recapitulation of cellular and tissue ultrastructure, immune cell interactions, etc.

As used herein, the term "immune cell" includes cells that are of hematopoietic origin and that play a role in the immune response. Immune cells include lymphocytes, such as B cells and T cells; natural killer cells; myeloid cells, such as monocytes, macrophages, eosinophils, mast cells, basophils, and granulocytes.

Methods are provided for the culture of small amounts of clinical specimens. Samples of interest include human tissue, particularly cancer and other lesions, e.g. solid tumor microbiopsy samples such as needle or fine needle aspirate. Samples may be taken at a single timepoint, or may be taken at multiple timepoints. Samples may be as small as $10^7$ cells, $10^6$ cells, $10^5$ cells, or less.

The phrase "mammalian cells" means cells originating from mammalian tissue. Typically, in the methods of the invention pieces of tissue are obtained surgically, e.g. biopsy, needle biopsy, etc. and minced to a size less than about 1 mm$^3$, and may be less than about 0.5 mm$^3$, or less than about 0.1 mm$^3$. "Mammalian" used herein includes human, equine, bovine, porcine, canine, feline, rodent, e.g. mice, rats, hamster, primate, etc. "Mammalian tissue cells" and "primary cells" have been used interchangeably.

"Ultrastructure" refers to the three-dimensional structure of a cell or tissue observed in vivo. For example, the ultrastructure of a cell may be its polarity or its morphology in vivo, while the ultrastructure of a tissue would be the arrangement of different cell types relative to one another within a tissue.

The term "candidate cells" refers to any type of cell that can be placed in co-culture with the tissue explants described herein. Candidate cells include without limitations, genetically engineered T cells including without limitation CAR-T cells, dendritic cells, phagocytic cells T cells, B cells, etc.

The term "candidate agent" means any oligonucleotide, polynucleotide, siRNA, shRNA, gene, gene product, peptide, antibody, small molecule or pharmacological compound that is introduced to an explant culture and the cells thereof as described herein to assay for its effect on the explants.

The term "contacting" refers to the placing of candidate cells or candidate agents into the explant culture as described herein. Contacting also encompasses co-culture of candidate cells with tissue explants for at least 1 hour, or more than 2 hrs or more than 4 hrs in culture medium prior to placing the tissue explants in a semi-permeable substrate. Alternatively, contacting refers to injection of candidate cells into the explant, e.g. into the lumen of an explant.

"Screening" refers to the process of either co-culturing candidate cells with or adding candidate agents to the PDO culture described herein and assessing the effect of the candidate cells or candidate agents on the PDO, including without limitation immune cells present in the PDO. The effect may be assessed by assessing any convenient parameter, e.g. phenotypic changes, protein expression, mRNA expression, etc.

Cancer immunotherapy is the use of the immune system to treat cancer. Immunotherapies can be categorized as active, passive or hybrid (active and passive). These approaches exploit the fact that cancer cells often have molecules on their surface that can be detected by the immune system, known as tumor-associated antigens (TAAs); they are often proteins or other macromolecules (e.g. carbohydrates).

Active immunotherapy, which may be referred to as immune-oncology, directs the immune system to attack tumor cells by targeting TAAs. Passive immunotherapies enhance existing anti-tumor responses and include the use of monoclonal antibodies, lymphocytes and cytokines.

Immune Responsiveness Modulators. Immune checkpoint proteins are immune inhibitory molecules that act to decrease immune responsiveness toward a target cell, particularly against a tumor cell in the methods of the invention. Endogenous responses to tumors by T cells can be dysregulated by tumor cells activating immune checkpoints (immune inhibitory proteins) and inhibiting co-stimulatory receptors (immune activating proteins). The class of therapeutic agents referred to in the art as "immune checkpoint inhibitors" reverses the inhibition of immune responses through administering antagonists of inhibitory signals. Other immunotherapies administer agonists of immune costimulatory molecules to increase responsiveness. Antibodies blocking the interaction of CD47 and SIRP⊐ can enhance phagocytosis of tumor cells.

Immune-checkpoint receptors that have been most actively studied in the context of clinical cancer immunotherapy, cytotoxic T-lymphocyte-associated antigen 4 (CTLA4; also known as CD152) and programmed cell death protein 1 (PD1; also known as CD279)—are both inhibitory receptors. The clinical activity of antibodies that block either of these receptors implies that antitumor immunity can be enhanced at multiple levels and that combinatorial strategies can be intelligently designed, guided by mechanistic considerations and preclinical models.

CTLA4 is expressed exclusively on T cells where it primarily regulates the amplitude of the early stages of T cell activation. CTLA4 counteracts the activity of the T cell co-stimulatory receptor, CD28. CD28 and CTLA4 share identical ligands: CD80 (also known as B7.1) and CD86 (also known as B7.2). The major physiological roles of CTLA4 are downmodulation of helper T cell activity and enhancement of regulatory T (TReg) cell immunosuppressive activity. CTLA4 blockade results in a broad enhancement of immune responses. Two fully humanized CTLA4 antibodies, ipilimumab and tremelimumab, are in clinical testing and use. Clinically the response to immune-checkpoint blockers is slow and, in many patients, delayed up to 6 months after treatment initiation. In some cases, metastatic lesions actually increase in size on computed tomography (CT) or magnetic resonance imaging (MRI) scans before regressing. Anti-CTLA4 antibodies that antagonize this inhibitory immune function are very potent therapeutics but have significant side effects since this enables also T cell activity against the self that is usually inhibited through these inhibitory molecules and pathways.

CTLA4 is expressed on regulatory T cells that inhibit T cell activation and expansion and anti-CTLA4 antibodies block their inhibitory immunosuppressive function. As a result, anti-tumor T cells can be/stay activated and expand. One aspect of this effect is the inhibition of the inhibitory signaling pathway but another aspect is the depletion of regulatory T cells that express CTLA4. The depletion is mediated through ADCP, ADCC, and/or CDC.

Other immune-checkpoint proteins are PD1 and PDL1. Antibodies in current clinical use against these targets include nivolumab and pembrolizumab. The major role of PD1 is to limit the activity of T cells in peripheral tissues at the time of an inflammatory response to infection and to limit autoimmunity. PD1 expression is induced when T cells become activated. When engaged by one of its ligands, PD1 inhibits kinases that are involved in T cell activation. PD1 is highly expressed on $T_{Reg}$ cells, where it may enhance their proliferation in the presence of ligand. Because many tumors are highly infiltrated with $T_{Reg}$ cells, blockade of the PD1 pathway may also enhance antitumor immune responses by diminishing the number and/or suppressive activity of intratumoral $T_{Reg}$ cells.

The two ligands for PD1 are PD1 ligand 1 (PDL1; also known as B7-H1 and CD274) and PDL2 (also known as B7-DC and CD273). The PD1 ligands are commonly upregulated on the tumor cell surface from many different human tumors. On cells from solid tumors, the major PD1 ligand that is expressed is PDL1. PDL1 is expressed on cancer cells and through binding to it's receptor PD1 on T cells it inhibits T cell activation/function. Therefore, PD1 and PDL1 blocking agents can overcome this inhibitory signaling and maintain or restore anti-tumor T cell function.

PDL1 is expressed on cancer cells and through binding to its receptor PD1 on T cells it inhibits T cell activation/function. Therefore, PD1 and PDL1 blocking agents can overcome this inhibitory signaling and maintain or restore anti-tumor T cell function. However, since PDL1 is expressed on tumor cells, antibodies that bind and block PDL1 can also enable ADCP, ADCC, and CDC of tumor cells. Anti-CD47 agents can synergize with targeted monoclonal antibodies and enhance their potency to stimulate ADCP and ADCC.

Lymphocyte activation gene 3 (LAG3; also known as CD223), 2B4 (also known as CD244), B and T lymphocyte attenuator (BTLA; also known as CD272), T cell membrane protein 3 (TIM3; also known as HAVcr2), adenosine A2a receptor (A2aR) and the family of killer inhibitory receptors have each been associated with the inhibition of lymphocyte activity and in some cases the induction of lymphocyte anergy. Antibody targeting of these receptors can be used in the methods of the invention.

LAG3 is a CD4 homolog that enhances the function of $T_{Reg}$ cells. LAG3 also inhibits $CD8^+$ effector T cell functions independently of its role on $T_{Reg}$ cells. The only known ligand for LAG3 is MHC class II molecules, which are expressed on tumor-infiltrating macrophages and dendritic cells. LAG3 is one of various immune-checkpoint receptors that are coordinately upregulated on both $T_{Reg}$ cells and anergic T cells, and simultaneous blockade of these receptors can result in enhanced reversal of this anergic state relative to blockade of one receptor alone. In particular, PD1 and LAG3 are commonly co-expressed on anergic or exhausted T cells. Dual blockade of LAG3 and PD1 synergistically reversed anergy among tumor-specific $CD8^+$ T cells and virus-specific $CD8^+$ T cells in the setting of chronic infection. LAG3 blocking agents can overcome this inhibitory signaling and maintain or restore anti-tumor T cell function.

TIM3 inhibits T helper 1 ($T_H1$) cell responses, and TIM3 antibodies enhance antitumor immunity. TIM3 has also been reported to be co-expressed with PD1 on tumor-specific $CD8^+$ T cells. Tim3 blocking agents can overcome this inhibitory signaling and maintain or restore anti-tumor T cell function.

BTLA is an inhibitory receptor on T cells that interacts with TNFRSF14. $BTLA^{hi}$ T cells are inhibited in the presence of its ligand. The system of interacting molecules is complex: CD160 (an immunoglobulin superfamily member) and LIGHT (also known as TNFSF14), mediate inhibitory and co-stimulatory activity, respectively. Signaling can be bidirectional, depending on the specific combination of interactions. Dual blockade of BTLA and PD1 enhances antitumor immunity.

A2aR, the ligand of which is adenosine, inhibits T cell responses, in part by driving CD4$^+$ T cells to express FOXP3 and hence to develop into $T_{Reg}$ cells. Deletion of this receptor results in enhanced and sometimes pathological inflammatory responses to infection. A2aR can be inhibited either by antibodies that block adenosine binding or by adenosine analogues.

Agents that agonize an immune costimulatory molecule are also useful in the screening methods of the invention. Such agents include agonists or CD40 and OX40. CD40 is a costimulatory protein found on antigen presenting cells (APCs) and is required for their activation. These APCs include phagocytes (macrophages and dendritic cells) and B cells. CD40 is part of the TNF receptor family. The primary activating signaling molecules for CD40 are IFNγ and CD40 ligand (CD40L). Stimulation through CD40 activates macrophages. OX40 (CD134) is a member of the TNFR superfamily and expressed on T cells. Molecules that bind OX40 can stimulate proliferation and differentiation of T cells.

Other immuno-oncology agents that can be screened according to the methods described herein include antibodies specific for chemokine receptors, including without limitation anti-CCR4 and anti-CCR2. Anti CCR4 (CD194) antibodies of interest include humanized monoclonal antibodies directed against C-C chemokine receptor 4 (CCR4) with potential anti-inflammatory and antineoplastic activities. Exemplary is mogamulizumab, which selectively binds to and blocks the activity of CCR4, which may inhibit CCR4-mediated signal transduction pathways and, so, chemokine-mediated cellular migration and proliferation of T cells, and chemokine-mediated angiogenesis. In addition, this agent may induce antibody-dependent cell-mediated cytotoxicity (ADCC) against CCR4-positive T cells. CCR4, a G-coupled-protein receptor for C-C chemokines such MIP-1, RANTES, TARC and MCP-1, is expressed on the surfaces of some types of T cells, endothelial cells, and some types of neurons. CCR4, also known as CD194, may be overexpressed on adult T-cell lymphoma (ATL) and peripheral T-cell lymphoma (PTCL) cells.

Anti-CCR2 (CD192) Ab. CCR2 is expressed on inflammatory macrophages that can be found in various inflammatory conditions, e.g. rheumatoid arthritis; and have also been identified as expressed on tumor promoting macrophages. Chemokines that bind to CCR2, e.g. CCL2, can recruit and activate the inflammatory macrophages. Inhibiting the chemokine signaling through CCR2 with anti-CCR2 antibodies may result in lower frequencies of undesirable autoimmune or tumor promoting macrophages through inhibition of recruiting or antibody dependent depletion, resulting in mitigation of autoimmune diseases like rheumatoid arthritis, or inhibition of tumor growth or metastasis. CCR2 is also expressed on regulatory T cells, and the CCR2 ligand, CCL2, mediates recruitment of regulatory T cells into tumors. Regulatory T cells suppress a response for anti-tumor T cells and thus their inhibition or depletion is desired.

Other active cellular therapies that can be screened by the methods described herein may involve the removal of immune cells from the PDO. Those specific for the tumor are cultured and returned to the patient where they attack the tumor. Cell types that can be used in this way are natural killer cells, lymphokine-activated killer cells, cytotoxic T cells and dendritic cells.

Alternatively adoptive T-cell therapy can be screened, e.g. in a form of passive immunization by the transfer of T-cells. Multiple ways of producing and obtaining tumor targeted T-cells have been developed. T-cells specific to a tumor antigen can be removed from a tumor sample (TILs) or filtered from blood. Subsequent activation and culturing is performed ex vivo, with the results reinfused. Activation can take place through gene therapy, or by exposing the T cells to tumor antigens.

Cytokines that potentially modulate immune responses can also be screened. The tumor often employs them to allow it to grow and reduce the immune response. These immune-modulating effects allow them to be used as drugs to provoke an immune response. Two commonly used cytokines are interferons and interleukins.

Many immuno-oncology agents are antibodies. As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies. The term "antibody" also includes antigen binding forms of antibodies, including fragments with antigen-binding capability (e.g., Fab', F(ab')$_2$, Fab, Fv and rIgG. The term also refers to recombinant single chain Fv fragments (scFv). The term antibody also includes bivalent or bispecific molecules, diabodies, triabodies, and tetrabodies.

Selection of antibodies may be based on a variety of criteria, including selectivity, affinity, cytotoxicity, etc. The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background. In general, antibodies of interest bind antigens on the surface of target cells in the presence of effector cells (such as natural killer cells or macrophages). Fc receptors on effector cells recognize bound antibodies.

An antibody immunologically reactive with a particular antigen can be generated by recombinant methods such as selection of libraries of recombinant antibodies in phage or similar vectors, or by immunizing an animal with the antigen or with DNA encoding the antigen. Methods of preparing polyclonal antibodies are known to the skilled artisan. The antibodies may, alternatively, be monoclonal antibodies. Monoclonal antibodies may be prepared using hybridoma methods. In a hybridoma method, an appropriate host animal is typically immunized with an immunizing agent to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell.

Antibodies also exist as a number of well-characterized fragments produced by digestion with various peptidases. Thus pepsin digests an antibody below the disulfide linkages in the hinge region to produce F(ab')$_2$, a dimer of Fab which itself is a light chain joined to $V_H$-$C_{H1}$ by a disulfide bond. The F(ab')$_2$ may be reduced under mild conditions to break the disulfide linkage in the hinge region, thereby converting the F(ab')$_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries.

Antibodies of interest may be tested for their ability to induce ADCC (antibody-dependent cellular cytotoxicity) or ADCP (antibody dependent cellular phagocytosis). Antibody-associated ADCC activity can be monitored and quantified through detection of either the release of label or lactate dehydrogenase from the lysed cells, or detection of reduced target cell viability (e.g. annexin assay). Assays for apoptosis may be performed by terminal deoxynucleotidyl transferase-mediated digoxigenin-11-dUTP nick end labeling (TUNEL) assay (Lazebnik et al., Nature: 371, 346 (1994). Cytotoxicity may also be detected directly by detection kits known in the art, such as Cytotoxicity Detection Kit from Roche Applied Science (Indianapolis, Ind.).

Other types of immune modulators include non-antibody entities such as polypeptides, nucleic acid-based entities such as CpG or DNA or RNA aptamers, small molecule chemical compounds and the like. These all could be tested in the organoid system.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell. Many types of cancers are known to those of skill in the art, including solid tumors such as carcinomas, sarcomas, glioblastomas, melanomas, lymphomas, myelomas, etc. Examples of cancer include but are not limited to, ovarian cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

The term "cancer" is not limited to any stage, grade, histomorphological feature, invasiveness, aggressiveness or malignancy of an affected tissue or cell aggregation. In particular stage 0 cancer, stage I cancer, stage II cancer, stage III cancer, stage IV cancer, grade I cancer, grade II cancer, grade III cancer, malignant cancer and primary carcinomas are included.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as ovarian cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence. The present methods allow prediction of whether a patient will be responsive to a therapy of interest.

As used herein, the terms "treatment," "treating," and the like, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment,"

as used herein, may include treatment of a tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

Treating may refer to any indicia of success in the treatment or amelioration or prevention of an cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with cancer or other diseases. The term "therapeutic effect" refers to the reduction, elimination, or prevention of the disease, symptoms of the disease, or side effects of the disease in the subject.

Methods

Culture systems and methods are provided for culture of solid tumors, including stromal and immune cells associated with the tumors in vivo. The cultures can be maintained for up to 5 days, up to 7 days, up to 10 days, up to 15 days, up to 21 days, up to 28 days, or more. In some embodiments, tissue, i.e. primary tissue, is obtained from a solid tumor. The tumor tissue may be from any mammalian species, e.g. human, equine, bovine, porcine, canine, feline, rodent, e.g. mice, rats, hamster, primate, etc.

Tumor tissue may be obtained by any convenient method, e.g. by biopsy, e.g. during endoscopy, during surgery, by needle, etc., and is typically obtained as aseptically as possible. Upon removal, tissue is immersed in ice-cold buffered solution, e.g. PBS, Ham's F12, MEM, culture medium, etc. Pieces of tissue may be minced to a size less than about 1 $mm^3$, and may be less than about 0.5 $mm^3$, or less than about 0.1 $mm^3$. The minced tissue is mixed with a gel substrate, e.g. a collagen gel solution, e.g. Cellmatrix type I-A collagen (Nitta Gelatin Inc.); a matrigel solution, etc. Subsequently, the tissue-containing gel substrate is layered over a layer of gel (a "foundation layer") in a container with a lower semi-permeable support, e.g. a membrane, supporting the foundation gel layer, and the tissue-containing gel substrate is allowed to solidify. This container is placed into an outer container containing a suitable medium, for example HAMs F-12 medium supplemented with fetal calf serum (FCS) at a concentration of from about 1 to about 25%, usually from about 5 to about 20%, etc.

The arrangement described above allows nutrients to travel from the bottom, through the membrane and the foundation gel layer to the gel layer containing the tissue. The level of the medium is maintained such that the top part of the gel, i.e. the gel layer containing the explants, is not submerged in liquid but is exposed to air. Thus the tissue is grown in a gel with an air-liquid interface. A description of an example of an air-liquid interface culture system is provided in Ootani et al. in Nat Med. 2009 June; 15(6):701-6, the disclosure of which is incorporated herein in its entirety by reference. The air-liquid interface organoid cultures could be moved into other formats such as multi-wells for screening or in submerged 2D or 3D geometries where the cells are placed underneath the tissue culture medium.

The continued growth of the PDO may be confirmed by any convenient method, e.g. phase contrast microscopy, stereomicroscopy, histology, immunohistochemistry, electron microscopy, etc. In some instances, cellular ultrastructure and multi-lineage differentiation may be assessed. Ultrastructure of the intestinal explants in culture can be determined by performing Hematoxylin-eosin staining, PCNA staining, electron microscopy, and the like using methods known in the art.

Experimental modifications may be made by any method known in the art, for example, as described below with regard to methods for providing candidate agents that are nucleic acids, polypeptides, small molecules, viruses, etc. to explants and the cells thereof for screening purposes.

Screening Methods

Methods and culture systems are provided for screening candidate agents or cells for an activity of interest. In these methods, candidate agents or cells are screened for their effect on cells in the PDO of the invention, including without limitation immune cells associated with the tumor.

The effect of an agent or cells, e.g. an immunotherapeutic agent, is determined by adding the agent or cells to the cells of the cultured explants as described herein, usually in conjunction with a control culture of cells lacking the agent or cells. The effect of the candidate agent or cell is then assessed by monitoring one or more output parameters. Parameters are quantifiable components of explants or the cells thereof, particularly components that can be accurately measured, in some instances in a high throughput system. For example, a parameter of the explant may be the growth, differentiation, survival, gene expression, proteome, phenotype with respect to markers etc. of the explant or the cells thereof, e.g. any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Candidate agent or cells can be added to the cells within the intact organoid. In other embodiments, the organoids are dissociated, and candidate agent or cells is added to the dissociated cells. The cells may be freshly isolated, cultured, genetically altered as described above; or the like. The cells may be environmentally induced variants of clonal cultures: e.g. split into independent cultures and grown into organoids under distinct conditions, for example with or without pathogen; in the presence or absence of other cytokines or combinations thereof. The manner in which cells respond to an agent, particularly a pharmacologic agent, including the timing of responses, is an important reflection of the physiologic state of the cell.

Candidate agents of interest for screening include known and unknown compounds that encompass numerous chemical classes, primarily organic molecules, for example antibodies, cytokines, etc. genetic sequences, etc. An important aspect of the invention is to evaluate candidate agents to predict patient responsiveness to immune-oncology agents.

In some cases, the candidate polypeptide agents to be screened are antibodies. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The specific or selective fit of a given structure and its specific epitope is sometimes referred to as a "lock and key" fit. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammal, chicken, other avians, etc., are considered to be "antibodies." Antibodies utilized in the present invention may be either polyclonal antibodies or monoclonal antibodies. Antibodies are typically provided in the media in which the cells are cultured.

Candidate agents may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents are screened for biological activity by adding the agent to at least one and usually a plurality of explant or cell samples, usually in conjunction with explants not contacted with the agent. The change in parameters in response to the test agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow-through method. Alternatively, the agents can be injected into the explant, e.g. into the lumen of the explant, and their effect compared to injection of controls.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the growth rate.

In some embodiments, a candidate agent is screened for activity that is anti-tumorigenic (i.e. inhibiting cancer initiation) or anti-tumoral (i.e. inhibiting cancer progression, e.g. proliferation, invasion, metastasis). In such embodiments, the explant culture includes cancer cells, including cells suspected of being cancer stem cells. Assessment of anti-tumor activity may include measurements of one or more parameters including explant growth, the rate or extent of cell proliferation, the rate or extent of cell death, etc. Assessment of anti-tumor activity may also include analysis of markers of immune cell activation (which include but are not limited to IFN-$\gamma$, granzyme, perforin, etc), expansion or alteration of immune cell populations (T, B, NK, monocyte/macrophage, dendritic cells, myeloid-derived suppressor cells), tumor cell death tumor phagocytosis and the like. Immune cells could be isolated and/or analyzed by any number of means including FACS, CyTOF, MIBI, multiplexed immunohistochemistry, quantitative RT-PCR, Luminex or others.

The following examples are put forth so as to provide those of ordinary skill in the art with a complete disclosure and description of how to make and use the subject invention, and are not intended to limit the scope of what is regarded as the invention.

EXPERIMENTAL

Modeling Tumor Immunity Using Patient Derived Organoids

In vitro modeling of cancer is substantially challenged by the need to recapitulate not only neoplastic cells but also the diverse cellular components of the tumor microenvironment (TME). Recent in vitro models growing primary human tumors as 3-dimensional spheroids are composed exclusively of epithelial cells, a reductionist approach that does not recapitulate higher-order phenomena involving stromal and/or immune interactions 1-4. Despite recent clinical successes in cancer immunotherapy, the co-culture of primary tumor epithelium with its endogenous tumor-infiltrating lymphocytes (TI Ls) has been particularly intractable.

Here, we describe the successful propagation of human clinical tumor biopsies as Patient-Derived Organoids (PDOs) characterized by the en bloc culture of primary tumor epithelium together with their native stromal and immune compartments without reconstitution. Using a single 3-dimensional air-liquid interface methodology, we generated 128 unique PDO cultures from diverse human neoplasms that accurately recapitulated clinical pathology upon histologic and large-scale mutational analysis. Immunophenotyping of additional non-small cell lung carcinoma (NSCLCa), melanoma, and renal cell carcinoma (RCC) PDO cultures revealed the preservation of endogenous immune subsets including CD3+CD8+PD1+ TILs, $T_{helper}$, B and NK cells amongst the tumor epithelium with additional TIL expansion upon IL-2 supplementation. Crucially, the immunotherapeutic PD-1 antibody nivolumab induced T-cell activation and cytolytic activity in a subset of PDO cultures, indicating successful in vitro recapitulation of immune checkpoint blockade and anti-tumor immunity. These tumor PDO models, culturing tumor epithelium with endogenous immune/non-immune stroma as a holistic unit, should facilitate the in vitro investigation of human tumor immunity with application to modeling patient immunotherapy responses in a clinical setting.

Figure 1B:
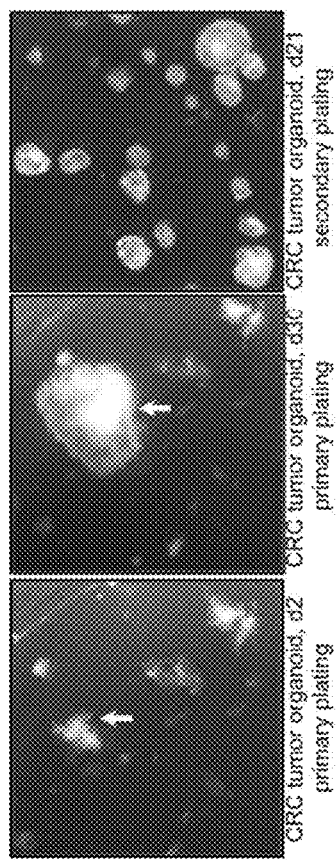
Figure 1C:
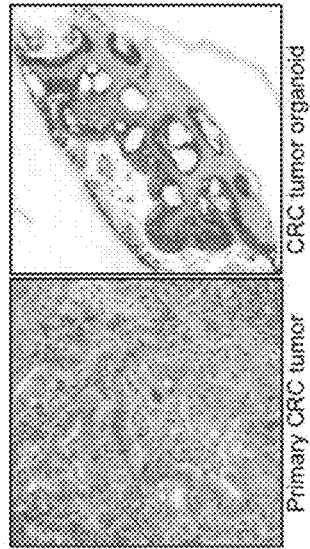

We established PDO cultures from primary and metastatic tumors obtained from surgical resection procedures by plating mechanically dissociated tumor fragments in a Type I collagen matrix using an air-liquid interface (ALI) culture system (FIG. 1a). Tumor fragments expanded to form organoids, which could be cultured for extended periods and expanded through passage and secondary plating (FIG. 1b). PDOs displayed striking recapitulation of histological architecture of the tumors from which they were derived (FIG. 1c), including cribriform growth, desmoplasia, and intraluminal necrosis. Further, blinded histological analysis of a subset of PDO cultures by a clinical pathologist identified the tumor subtype and grade of the original tumors with a 90% success rate. Importantly, PDOs preserved stroma as characterized by vimentin+ cells. PDO cultures could also be isolated from the collagen matrix and cryopreserved without the loss of stromal cells or architecture allowing precious viable patient cultures to be maintained indefinitely (FIG. 1E). In selected cases. patient-derived organoids could also be cryopreserved and re-propagated in vitro as organoids having tumor epithelial and stromal components. Alternatively, PDOs could be xenografted into immunocompromised mice to generate transplantable models of cancer progression, and then re-derived as organoid cultures thereafter (FIG. 1F).

Figures 2A, 2B:
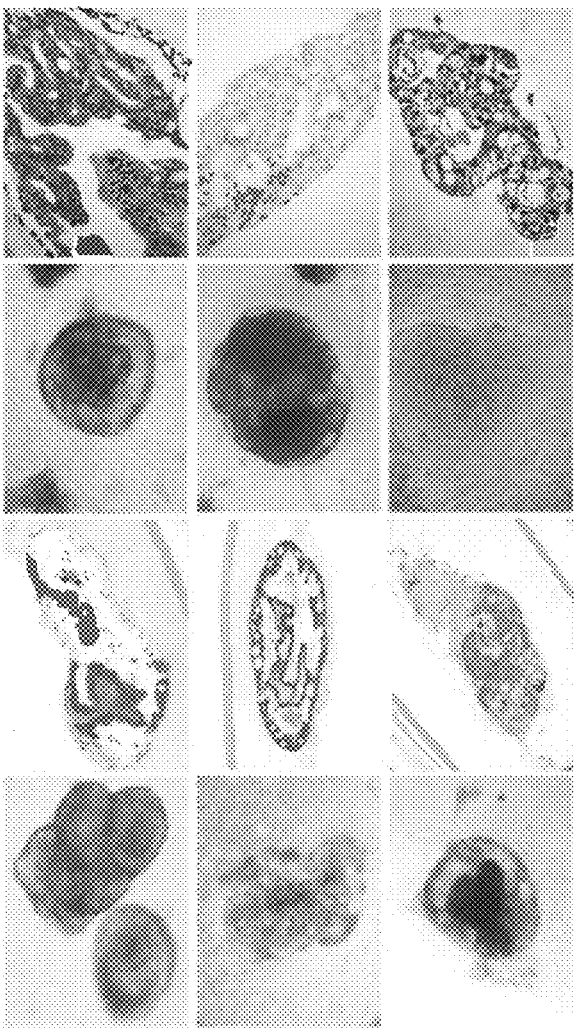
FIG. 2A-2D. Establishment and characterization of PDOs from a wide range of tumor types.
Figure 2C:
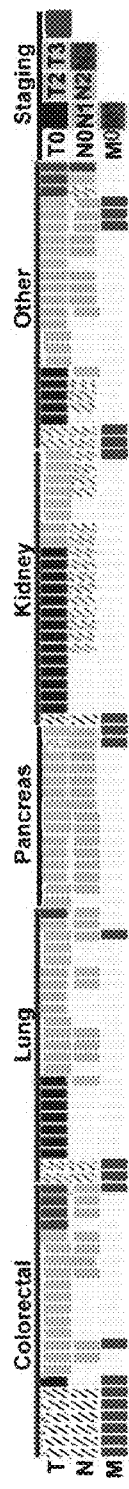
Figure 2D:
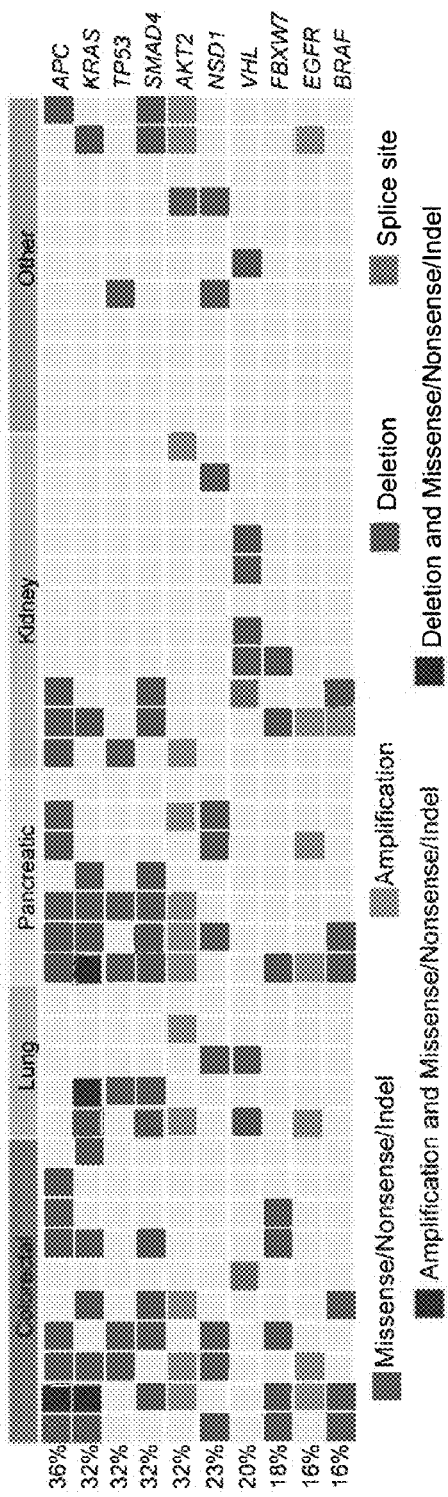

To illustrate the versatility of the air-liquid interface PDO culture method, we successfully established and characterized PDO cultures from 130 individual patient tumors representing 21 distinct tissue sites and over 50 unique disease subtypes (FIG. 2a). These PDOs included more common tumor sites well represented in cell line collections such as colon, pancreas, and lung, as well as rarer subtypes such as bile duct and endometrium for which cell lines are not readily available (FIG. 2b). Additionally, PDOs were generated from a wide range of tumor stages and grades, illustrating the utility of the method for the study of early and late stage tumor progression (FIG. 2c). Targeted exome sequencing and copy-number variation analysis of PDOs revealed alterations consistent with previous large-scale sequencing studies[11-14] such as high rates of APC loss in colorectal adenocarcinoma, KRAS mutations in pancreatic and lung cancers, and VHL alterations in clear cell renal carcinoma (FIG. 2d).

Figure 3A:
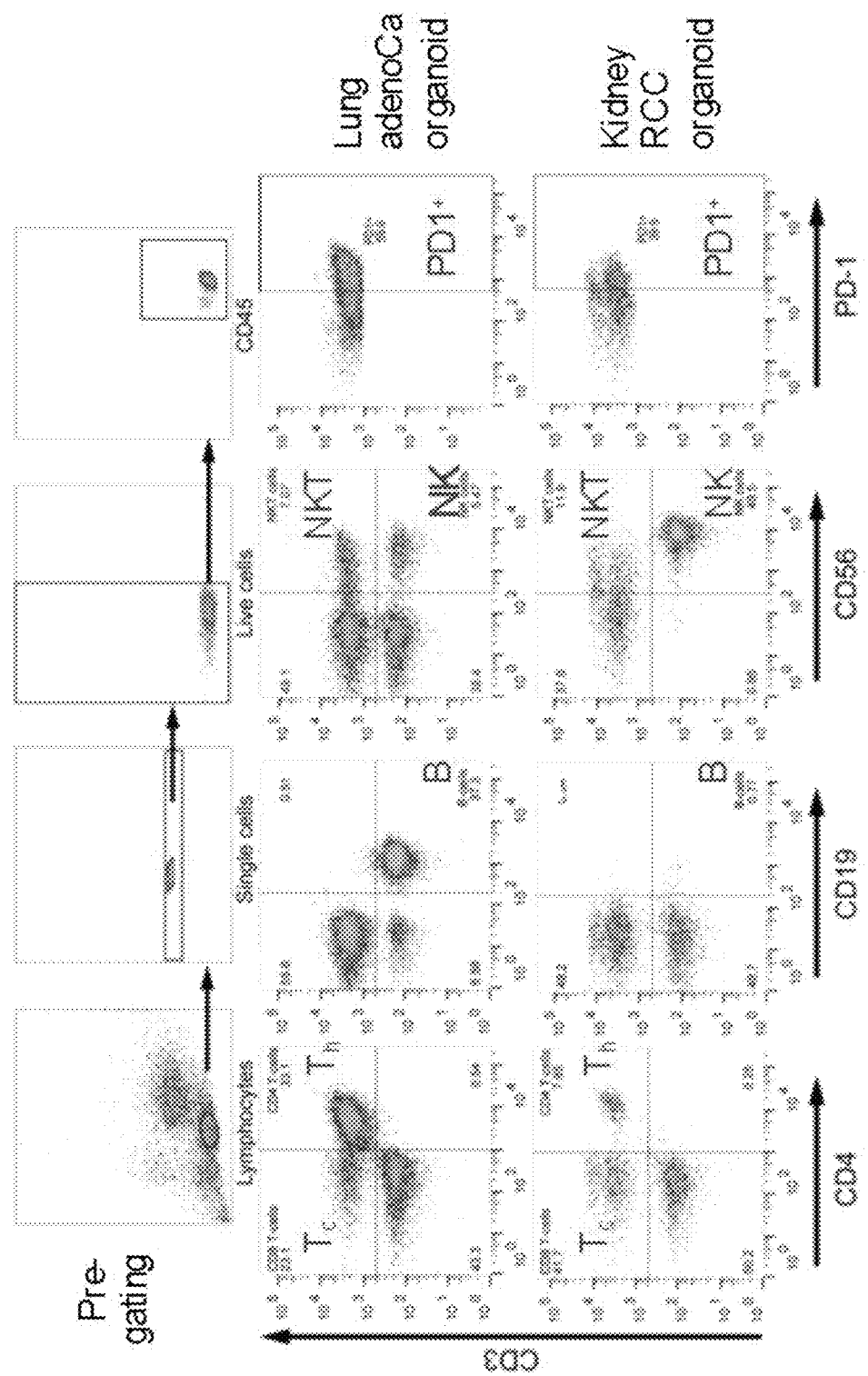
FIG. 3A-3G. PDOs contain TILs.
Figure 3B:
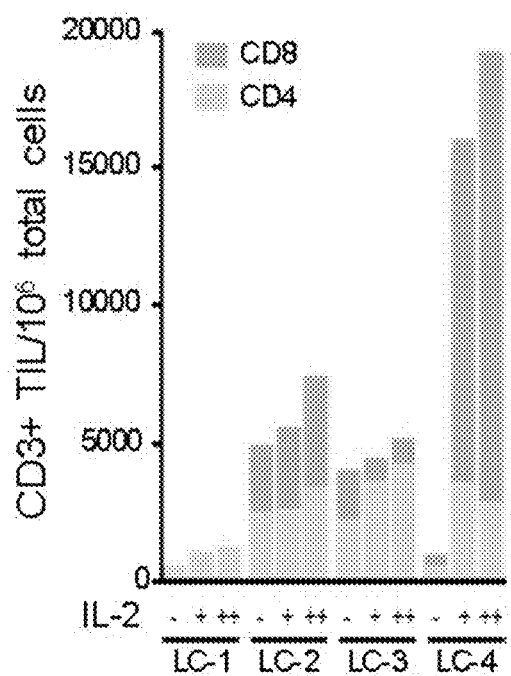
Figure 3C:
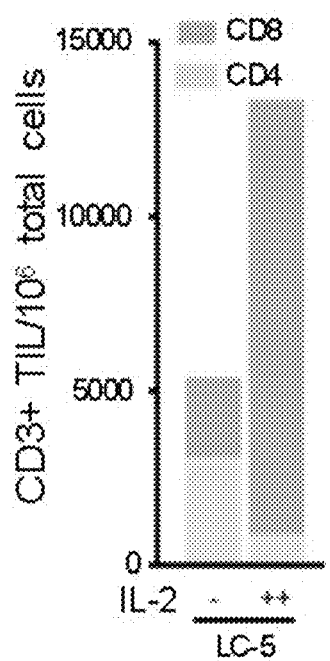
Figure 3E:
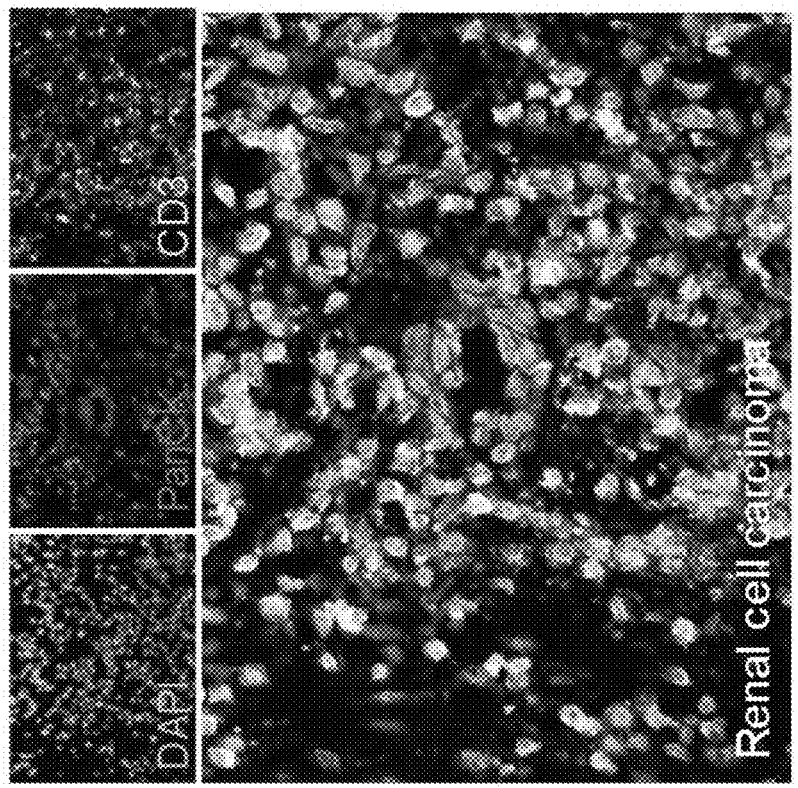
Figure 3D:
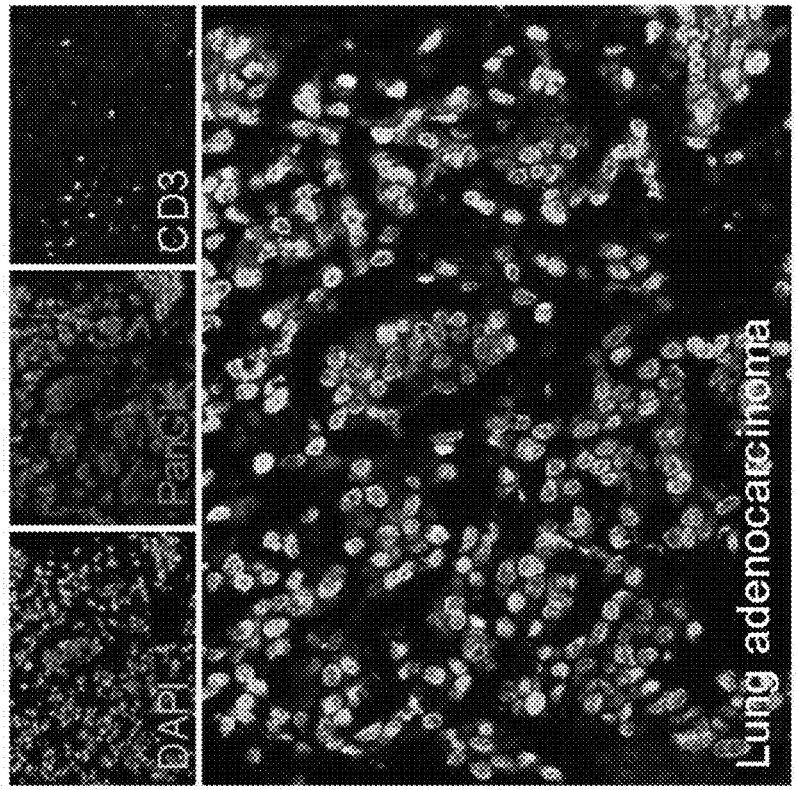
Figure 3F:
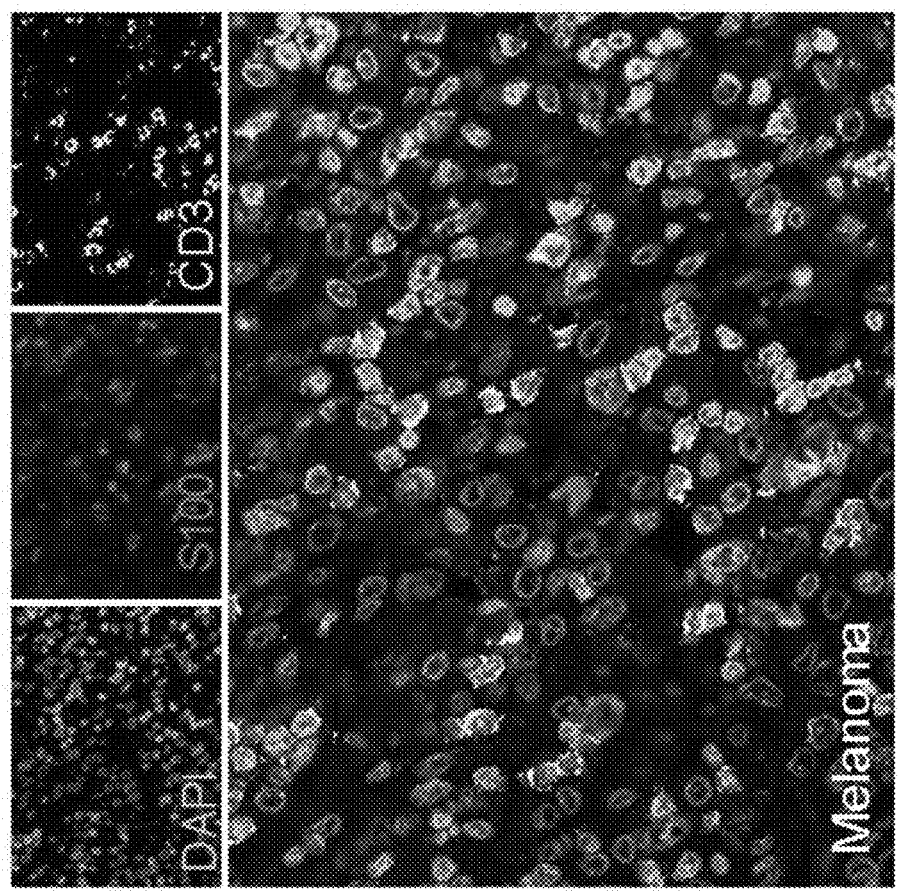
Figure 3G:
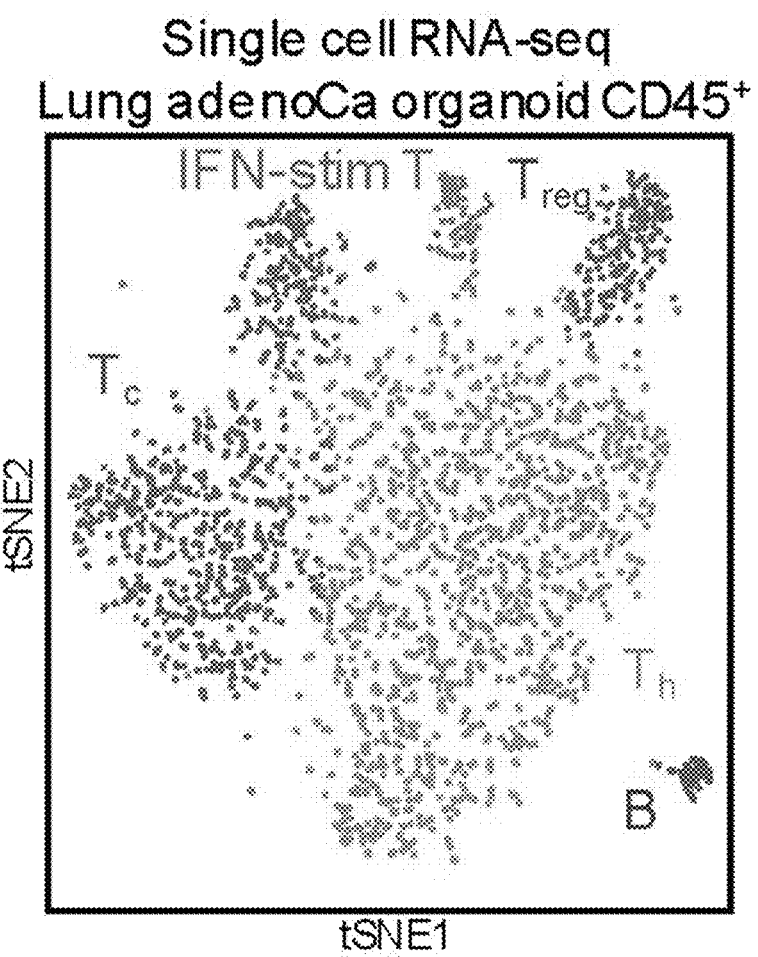
Figure 3G:
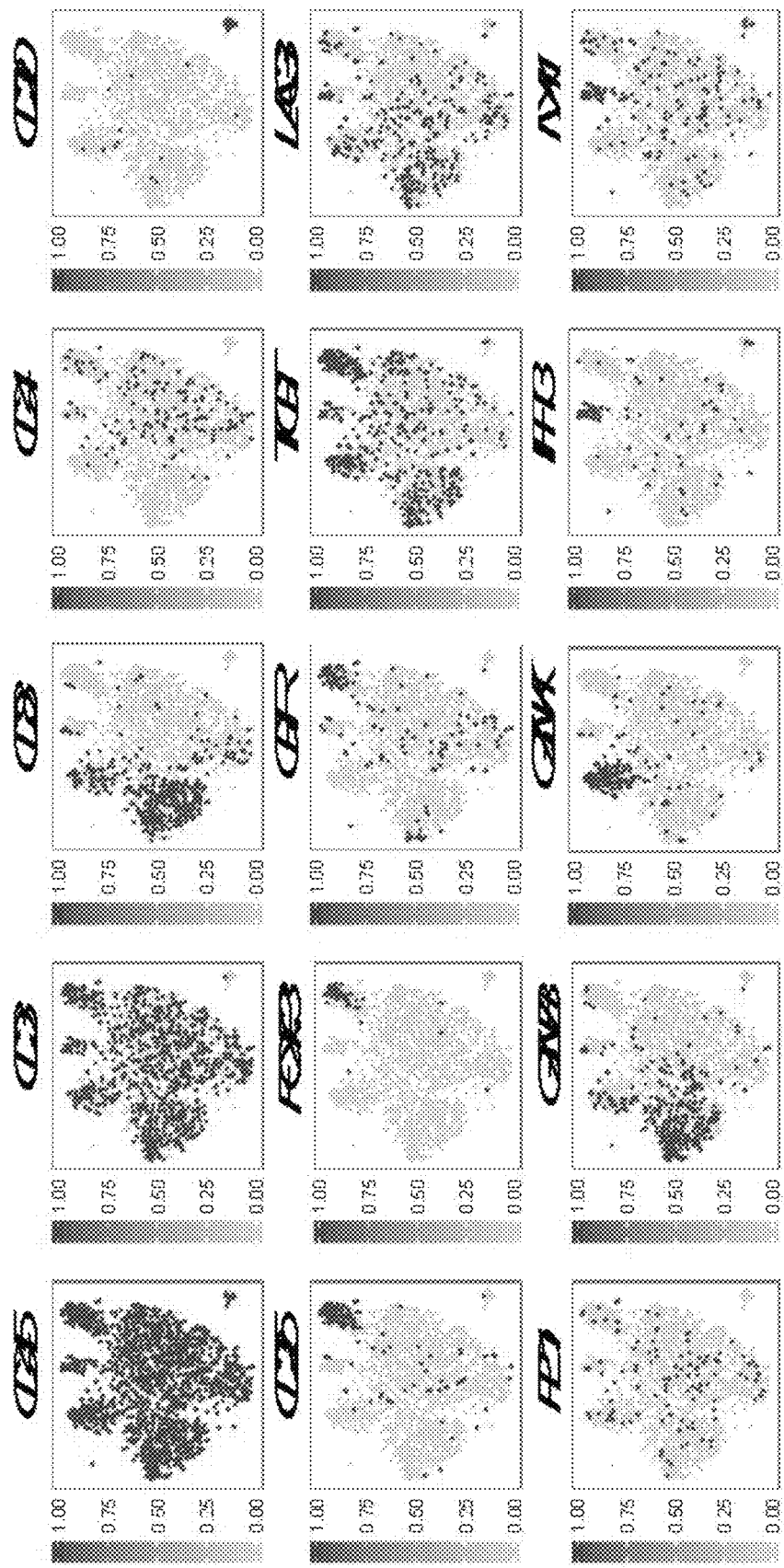

Given the presence of fibroblast stroma within ALI PDOs, we next sought to establish an analogous presence of immune cell components. Using this optimized protocol, FACS analysis of dissociated PDOs revealed numerous immune cell types including natural killer (NK) and natural killer T (NKT) cells, B-cells, and CD4 and CD8 positive T-cells (FIG. 3a). Additionally, we identified a subset of PDO-infiltrating CD3+CD8+ T-cells also positive for the immune checkpoint surface receptor programmed cell death protein-1 (PD-1) by FACS (FIG. 3a). Longitudinal FACS analysis of PDO cultures showed robust T-cell populations persisting for up to 28 days in culture (longest time point examined) and addition of the cytokine interleukin-2 (IL-2) to organoid culture medium could significantly expand PDO T-cell populations (FIG. 3b,c). Immunofluorescence staining of formalin-fixed PDO cultures identified PD-1 positive T-cells in close proximity to tumor epithelial cells within organoids (FIG. 3d-f). Similarly, distinct immune populations could be detected with PDOs by single cell RNA-seq, including $T_{helper}$, $T_{cytotoxic}$, and $T_{reg}$ (FIG. 3g).

The ability of ALI organoids to preserve primary tumor epithelium en bloc with their endogenous TILs affords an unprecedented opportunity for human in vitro immunotherapy modeling. Human tumors and their corresponding PDO cultures each represent matched sets of primary human tumor cells and their cognate tumor antigen-reactive immune components. Thus, any successful functional demonstration of anti-tumor immunity within PDOs is obligately linked to testing patient-specific responses of endogenous infiltrating immune populations against a patient's own tumor cells. In particular, there is currently no precise method to robustly predict patient responses to immunotherapy[15]; for instance, current IHC-based diagnostic assays for the efficacy of PD-1/PD-L1 immune checkpoint blockade often fail to either correctly identify responders or exclude non-responders[16,17].

Figure 4A:
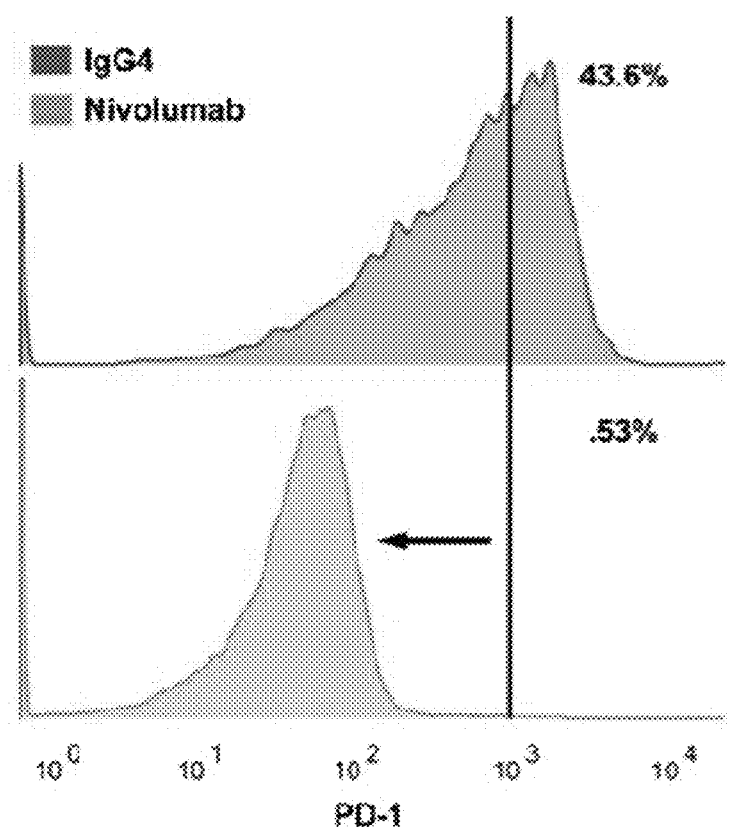
FIG. 4A-4C. Organoid Checkpoint Inhibitor (ORCHID) assay.
Figure 4B:
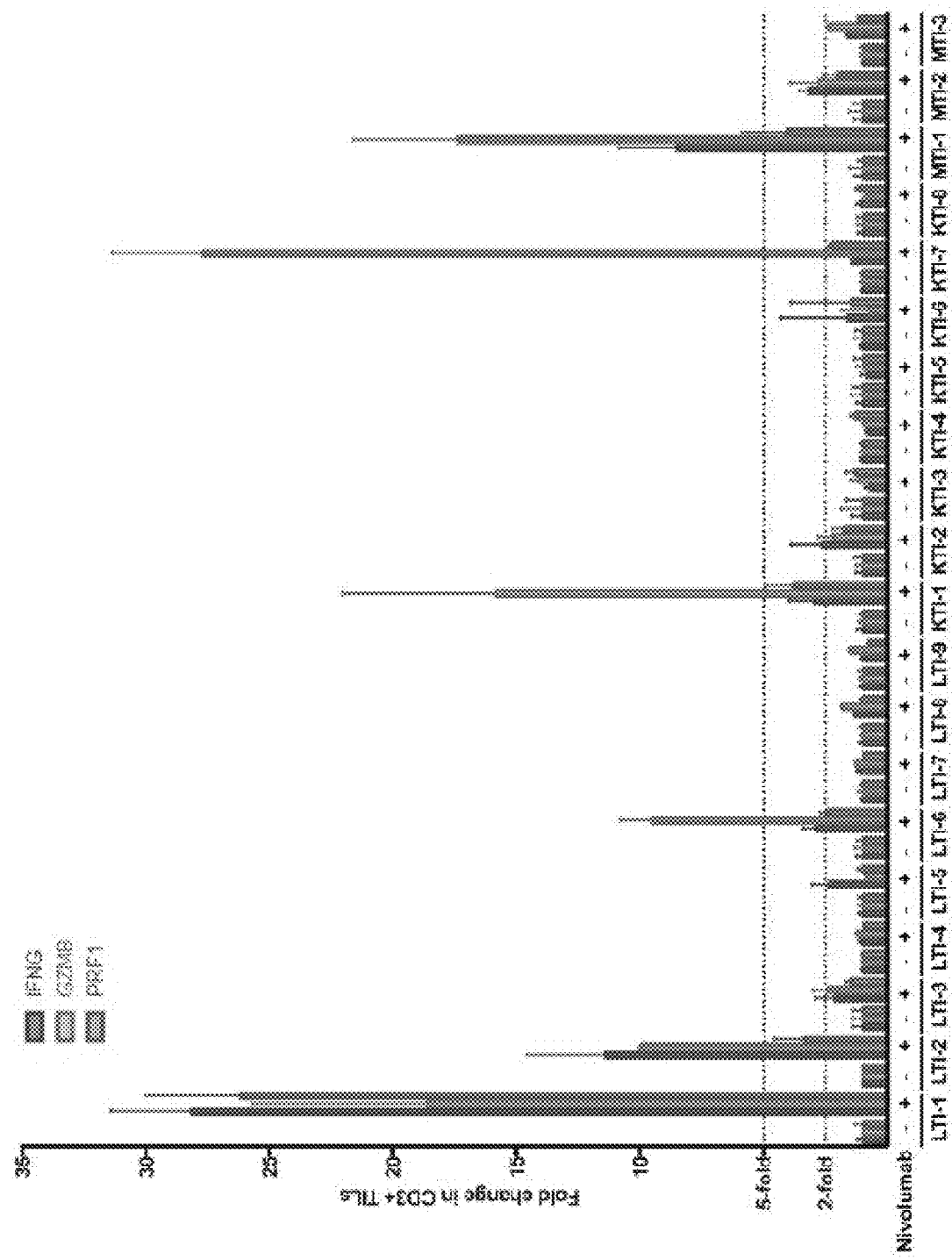
Figure 4C:
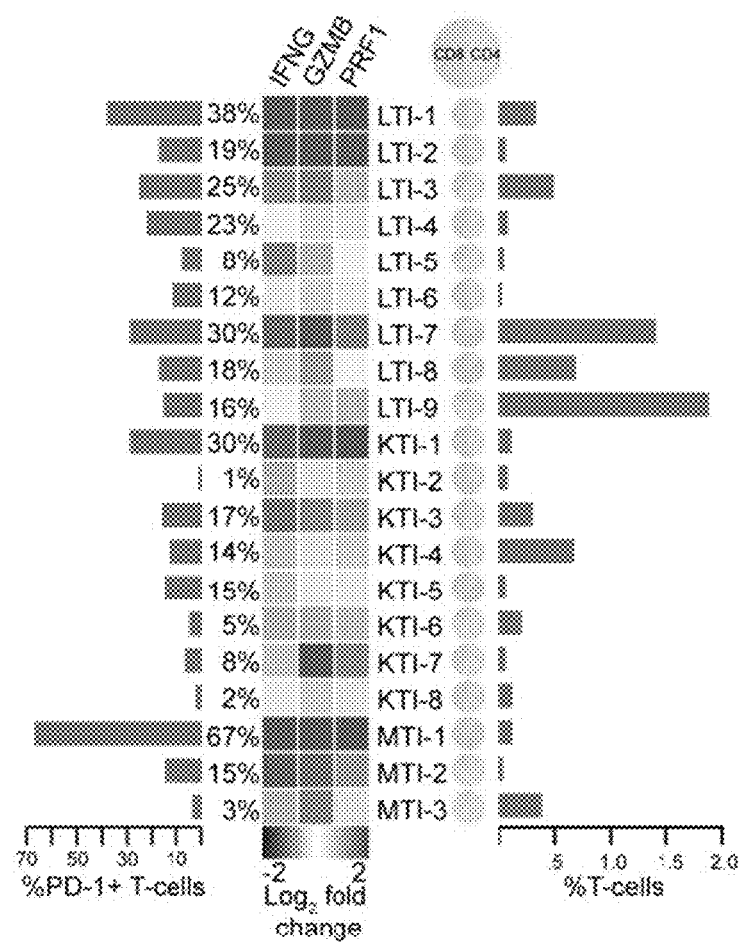

To this end, we developed ORCHID (Organoid Checkpoint Inhibitor Diagnostic), a functional assay to assess PDO response to checkpoint blockade immunotherapy within a clinically actionable 7 day time frame. We established PDO cultures from 20 distinct surgically-resected tumor biopsies representing the canonical immunotherapy-responsive neoplasms non-small cell lung cancer, renal cell carcinoma, and melanoma. PDO cultures were split into two triplicate groups receiving either 10 μg/ml of the therapeutic PD-1 blocking antibody nivolumab, or 10 μg/ml control human IgG4. After 7 days of treatment, organoid cultures were dissociated and immunophenotyped by FACS for T-cell populations, CD4/CD8 subsets and PD-1 positivity, with CD3-positive TILs undergoing further sorting for downstream analysis. Nivolumab-treated cultures exhibited a loss of PD-1 signal on CD3+ T cells by FACS, indicating quantitative in vitro saturation of TIL cell-surface PD-1 by nivolumab (FIG. 4a). Sorted CD3+ TILs, with and without in vitro PDO nivolumab treatment, were further subjected to quantitative real-time PCR analysis for markers of T-cell activation and cytolytic activity. Specifically, we assessed transcript levels of the $T_h1$ cytokine and T-cell activation marker interferon-gamma (IFNG), as well as the cytolytic markers Perforin-1 (PRF1) and Granzyme-b (GZMB), all of which are associated with response to PD-1/PD-L1 checkpoint blockade therapy[18]. Crucially, 6 of the 20 tumor samples subjected to the ORCHID assay responded to nivolumab treatment via high-grade induction (>5-fold) of IFNG, PRF1, and/or GZMB, within organoid FACS-sorted CD3+ TILs, denoting functional in vitro recapitulation of checkpoint inhibition (FIG. 4b). The TIL response to nivolumab spanned NSCLC, RCC and melanoma exhibited good concordance with rates of PD-1/PD-L1 checkpoint blockade response previously observed in clinical trials for NSCLC[17,19-21], RCC[22], and melanoma[23-26]. Further, the TIL response significantly correlated with PD-1 expression on organoid-infiltrating T-cells but was not correlated with CD4/CD8 ratio or T-cell frequency (percent of total cells) within organoids (FIG. 4c). Overall, the nivolumab stimulation of IFNG, PRF1 and GZMB within organoid TILs strongly indicated that PDOs can successfully recapitulate checkpoint inhibition between matched tumor cells and their endogenously infiltrating lymphocyte populations.

Provided herein is a robust organoid methodology facilitating in vitro study of the TME through the holistic co-culture of primary tumor epithelium with both immune and non-immune stromal elements. Such PDOs provide a substantial opportunity for human in vitro immunotherapy modeling via the unified en bloc culture of primary human tumor epithelium together with matched endogenous tumor-reactive TILs, as opposed to epithelial-only organoid models and reconstitution of peripheral blood or TIL populations with cancer cell lines.

The PDO system can be further extended to additional immune strategies targeting B cells, NK cells and macrophages that are also present in PDOs, or to parallel immunotherapy concepts such as CAR T cells. There is perhaps no higher current priority in oncology drug development than extending the substantial benefits of immunotherapy to larger patient subsets, since only ~20-30% of unstratified patients across solid tumor types respond to therapies targeting the PD-1/PD-L1 axis, and other immune-oncology targets. Thus, PDOs or analogous preclinical approaches facilitate basic studies into the mechanisms of tumor immunity, test novel immunotherapeutic agents and combinations, and predictively assess individualized patient responses to clinically approved immune therapies or combinations thereof, which are unrealized by current immunohistochemistry or neoantigen load metrics.

Patient-derived organoids can serve alongside traditional 2D culture and xenograft approaches as a bridge from bench to bedside, helping realize the promise of precision cancer therapy.

Methods

Human specimens. Tumor tissues were obtained through the Stanford Tissue Bank from patients undergoing surgical resection at Stanford University Medical Center (SUMC). All experiments utilizing human material were approved by SUMC's Institutional Review Board and performed under protocol #28908. Written informed consent for research was obtained from donors prior to tissue acquisition. Samples were confirmed to be tumor by pathological assessment at SUMC.

PDO culture. Tumor tissues were minced finely, washed twice in ADMEM/F12 (Invitrogen) containing 1× Normocin (InvivoGen), resuspended in Type I collagen gel (Trevigen), and layered in a double dish air-liquid culture system as previously described. Organoids were cultured in human organoid medium (ADMEM/F12 supplemented with 50% Wnt3a, RSPO1, Noggin-conditioned media (L-WRN, ATCC), HEPES (1 mM, Invitrogen), Glutamax (1×, Invitrogen), Nicotinamide (10 mM, Sigma), N-Acetylcysteine (1 mM, Sigma), B-27 without vitamin A (1×, Invitrogen), A83-01 (0.5 µM, Tocris), Pen-Strep Glutamine (1×, Invitrogen), Gastrin (10 nM, Sigma), SB-202190 (10 µM, Sigma), and EGF (50 ng/mL, Invitrogen). Organoids were passaged every 14-30 days by dissociation with 200 units $ml^{-1}$ collagenase IV (Worthington) at 37° C. for 30 min, followed by three 5-min washes with 100% FBS and replating at a 1:4 split into new air-liquid interface collagen gels. Additionally, in some cases, media was supplemented with IL-2 (Peprotech) at 600 or 6000 IU/mL.

ORCHID assay. Organoid cultures were established as above, and supplemented with organoid medium containing 10 µg/mL nivolumab (Bristol-Myers Squibb) or 10 µg/mL control human IgG4 (Abcam). Organoids were grown for 7 days, dissociated in 200 units $ml^{-1}$ collagenase IV (Worthington) at 37° C. for 30 min, washed twice in ADMEM/F12, and digested in Liberase-TL at 37° C. for 15 min. Samples were washed twice in ADMEM/F12, triturated with a P1000 pipet to dissociate further, and run over a 40 µM filter. Single cells were then pelleted, resuspended in 100 µL FACS Buffer (PBS plus 2 mM EDTA and 0.1% BSA) and stained for FACS. FACS staining cocktail contained 50 µL Brilliant Stain Buffer (BD), 10 µL anti-CD45 (2D1, BD), 10 µL anti-CD279 (PD-1 clone EH12.1, BD), 3 µL anti-CD-3 (UCHT1, BD), 3 µL anti-CD4 (RPA-T4, BD), and 10 µL 7-AAD (BD). An additional subset of samples also contained 3 µL anti-CD19 (SJ25C1, BD) and 3 µL anti-CD56 (B159, BD). T-cells were sorted on a BD Aria II flow cytometer into RNA extraction buffer, and RNA was extracted using the Arcturus PicoPure kit (Applied Biosystems). Extracted RNA was converted to cDNA using the iScript cDNA synthesis kit (Bio-Rad), and cDNA was subjected to 10-12 rounds of preamplification using SsoAdvanced PreAmp Supermix (Bio-Rad). cDNA was used for quantitative real-time PCR on a StepOnePlus instrument (Applied Biosystems) using TaqMan probe/primer sets for TBP, IFNG, GZMB and PRF1.

Histology. Organoids were fixed with 4% paraformaldehyde overnight, paraffin embedded and sectioned (4-5 µm) as previously described. Sections were deparaffinized and stained with H&E for the initial histology analysis. Immunofluorescence analysis was carried out using antibodies. Additionally, immunohistochemical analysis was performed for tumor-type specific markers by Stanford University Medical Center's Pathology Department using their clinical pipeline.

1. Boj S F, Hwang C I, Baker L A, et al. Organoid models of human and mouse ductal pancreatic cancer. Cell. 2015; 160(1-2):324-338.
2. Gao D, Vela I, Sboner A, et al. Organoid cultures derived from patients with advanced prostate cancer. Cell. 2014; 159(1):176-187.
3. Neal J T, Kuo C J. Organoids as Models for Neoplastic Transformation. Annu Rev Pathol. 2016; 11:199-220.
4. van de Wetering M, Francies H E, Francis J M, et al. Prospective derivation of a living organoid biobank of colorectal cancer patients. Cell. 2015; 161(4):933-945.
5. Junttila M R, de Sauvage F J. Influence of tumour micro-environment heterogeneity on therapeutic response. Nature. 2013; 501(7467):346-354.
6. Feder-Mengus C, Ghosh S, Reschner A, Martin I, Spagnoli G C. New dimensions in tumor immunology: what does 3D culture reveal? Trends in molecular medicine. 2008; 14(8):333-340.
7. Sutherland R M, MacDonald H R, Howell R L. Multicellular spheroids: a new model target for in vitro studies of immunity to solid tumor allografts. Journal of the National Cancer Institute. 1977; 58(6): 1849-1853.
8. Dangles-Marie V, Richon S, El-Behi M, et al. A three-dimensional tumor cell defect in activating autologous CTLs is associated with inefficient antigen presentation correlated with heat shock protein-70 down-regulation. Cancer research. 2003; 63(13):3682-3687.
9. Hirt C, Papadimitropoulos A, Mele V, et al. "In vitro" 3D models of tumor-immune system interaction. Advanced drug delivery reviews. 2014; 79-80:145-154.
10. Li X, Nadauld L, Ootani A, et al. Oncogenic transformation of diverse gastrointestinal tissues in primary organoid culture. Nat Med. 2014; 20(7):769-777.
11. Bailey P, Chang D K, Nones K, et al. Genomic analyses identify molecular subtypes of pancreatic cancer. Nature. 2016; 531(7592):47-52.
12. Cancer Genome Atlas N. Comprehensive molecular characterization of human colon and rectal cancer. Nature. 2012; 487(7407):330-337.

13. Cancer Genome Atlas Research N. Comprehensive molecular characterization of clear cell renal cell carcinoma. Nature. 2013; 499(7456):43-49.
14. Cancer Genome Atlas Research N. Comprehensive molecular profiling of lung adenocarcinoma. Nature. 2014; 511(7511):543-550.
15. Taube J M, Klein A, Brahmer J R, et al. Association of PD-1, PD-1 ligands, and other features of the tumor immune microenvironment with response to anti-PD-1 therapy. Clin Cancer Res. 2014; 20(19):5064-5074.
16. Carbognin L, Pilotto S, Milella M, et al. Differential Activity of Nivolumab, Pembrolizumab and MPDL3280A according to the Tumor Expression of Programmed Death-Ligand-1 (PD-L1): Sensitivity Analysis of Trials in Melanoma, Lung and Genitourinary Cancers. PLoS One. 2015; 10(6):e0130142.
17. Garon E B, Rizvi N A, Hui R, et al. Pembrolizumab for the treatment of non-small-cell lung cancer. N Engl J Med. 2015; 372(21):2018-2028.
18. Herbst R S, Soria J C, Kowanetz M, et al. Predictive correlates of response to the anti-PD-L1 antibody MPDL3280A in cancer patients. Nature. 2014; 515 (7528):563-567.
19. Borghaei H, Paz-Ares L, Horn L, et al. Nivolumab versus Docetaxel in Advanced Nonsquamous Non-Small-Cell Lung Cancer. N Engl J Med. 2015; 373(17):1627-1639.
20. Brahmer J, Reckamp K L, Baas P, et al. Nivolumab versus Docetaxel in Advanced Squamous-Cell Non-Small-Cell Lung Cancer. N Engl J Med. 2015; 373(2): 123-135.
21. Herbst R S, Baas P, Kim D W, et al. Pembrolizumab versus docetaxel for previously treated, PD-L1-positive, advanced non-small-cell lung cancer (KEYNOTE-010): a randomised controlled trial. Lancet. 2016; 387(10027): 1540-1550.
22. Motzer R J, Escudier B, McDermott D F, et al. Nivolumab versus Everolimus in Advanced Renal-Cell Carcinoma. N Engl J Med. 2015; 373(19):1803-1813.
23. Ribas A, Puzanov I, Dummer R, et al. Pembrolizumab versus investigator-choice chemotherapy for ipilimumab-refractory melanoma (KEYNOTE-002): a randomised, controlled, phase 2 trial. Lancet Oncol. 2015; 16(8):908-918.
24. Robert C, Long G V, Brady B, et al. Nivolumab in previously untreated melanoma without BRAF mutation. N Engl J Med. 2015; 372(4):320-330.
25. Robert C, Schachter J, Long G V, et al. Pembrolizumab versus Ipilimumab in Advanced Melanoma. N Engl J Med. 2015; 372(26):2521-2532.
26. Weber J S, D'Angelo S P, Minor D, et al. Nivolumab versus chemotherapy in patients with advanced melanoma who progressed after anti-CTLA-4 treatment (CheckMate 037): a randomised, controlled, open-label, phase 3 trial. Lancet Oncol. 2015; 16(4):375-384.

What is claimed is:

1. A method for determining responsiveness of a patient's tumor to an antibody that inhibits an immune checkpoint pathway, the method comprising: obtaining a tumor tissue sample comprising stromal and immune cells associated with the tumor; culturing the tumor tissue sample in a gel with an air-liquid interface to provide a patient specific organoid (PDO) with stromal and immune cell elements; contacting the PDO with a candidate antibody that inhibits an immune checkpoint pathway for a period of time sufficient to modulate immune cell activity; determining the effect of the candidate antibody on immune cell activity, wherein activation of immune cells is determined by measuring expression of mRNA or protein markers associated with immune activation, comprising IFNy, granzyme and perforin; wherein activation of immune cells relative to a control in the absence of the antibody that inhibits an immune checkpoint pathway is indicative the patient is responsive to the antibody.

2. The method of claim 1, wherein the immune cells comprise T cells.

3. The method of claim 1, wherein the immune cells comprise one or more of B cells, NK cells, dendritic cells, macrophages, myeloid derived suppressor cells and T cells.

4. The method of claim 1, wherein determining effect of the antibody on immune cells comprises dissociating the PDO culture and phenotyping the immune cells.

5. The method of claim 3, wherein the immune cells are sorted or analyzed by flow cytometry to determine the effect on a specific cell subset.

6. The method of claim 5 wherein the specific cell subset is a T cell subset.

7. The method of claim 1, wherein the preclinical efficacy of the antibody is determined.

8. The method of claim 1, further comprising the step of administering to the patient an antibody that the patient is determined to be responsive to.

9. A method for determining responsiveness of a patient's tumor to a candidate antibody that inhibits an immune checkpoint pathway, the method comprising: obtaining a tumor tissue sample comprising stroma cells associated with the tumor and endogenous tumor-infiltrating lymphocytes that are natively present in a given tumor; culturing the tumor tissue sample in a gel with an air-liquid interface to provide a patient specific organoid (PDO) with stromal and immune cell elements; contacting the PDO with a candidate antibody that inhibits an immune checkpoint pathway, for a period of time sufficient to modulate immune cell activity; determining the effect of the candidate antibody on immune cell activity by one or both of (i) dissociating the PDO culture and phenotyping tumor associated T lymphocytes present in the culture; and (ii) measuring expression of protein markers associated with T cell activation, wherein activation of T cells, relative to a control in the absence of the candidate antibody, is indicative the patient is responsive to the candidate antibody.

* * * * *